(12) United States Patent
Tokuda et al.

(10) Patent No.: US 9,523,752 B2
(45) Date of Patent: Dec. 20, 2016

(54) INTERFACE FOR MEDICAL IMAGING DEVICE

(75) Inventors: Junichi Tokuda, Boston, MA (US); Li Pan, Perry Hall, MD (US); Christine Lorenz, Frederick, MD (US)

(73) Assignee: The General Hospital Corporation, Boston, MA (US)

( * ) Notice: Subject to any disclaimer, the term of this patent is extended or adjusted under 35 U.S.C. 154(b) by 1246 days.

(21) Appl. No.: 13/480,214

(22) Filed: May 24, 2012

(65) Prior Publication Data
US 2013/0314085 A1 Nov. 28, 2013

(51) Int. Cl.
  *G01V 3/00* (2006.01)
  *G01R 33/54* (2006.01)
  *G01R 33/28* (2006.01)
  *A61B 10/02* (2006.01)

(52) U.S. Cl.
  CPC .......... *G01R 33/546* (2013.01); *G01R 33/543* (2013.01); *A61B 10/0233* (2013.01); *G01R 33/285* (2013.01)

(58) Field of Classification Search
  CPC .................................................. G01R 33/543
  USPC ................................ 324/309, 307, 318, 322
  See application file for complete search history.

(56) References Cited

U.S. PATENT DOCUMENTS

| | | | | |
|---|---|---|---|---|
| 5,512,827 A | * | 4/1996 | Hardy | G01R 33/54 324/307 |
| 6,275,721 B1 | * | 8/2001 | Darrow | G01R 33/54 324/318 |
| 6,512,373 B1 | * | 1/2003 | Griffin | G01R 33/4833 324/309 |
| 2010/0037182 A1 | * | 2/2010 | Biglieri | G01R 33/54 715/849 |
| 2016/0011285 A1 | * | 1/2016 | Griswold | G01R 33/286 600/411 |

OTHER PUBLICATIONS

Jung, Extinct HP TouchPad Resurrected for Use During Interventional MRI, http://www.medgadget.com/2011/12/extinct-hp-touchpad-resurrected-for-use-during-interventional-mri.html, Dec. 9, 2011, 3 pages.
MRI and the TouchPad, https://developer.palm.com/content/community/mri_and_the_touchpad.html, Copyright 2011 Hewlett-Packard Development Company, L.P., 5 pages.

* cited by examiner

*Primary Examiner* — Louis Arana
(74) *Attorney, Agent, or Firm* — Quarles & Brady LLP

(57) ABSTRACT

A system and method for modifying an imaging plane of a medical imaging device is presented. An electronic device includes a tilt sensor. The electronic device is configured to monitor a tilt of the electronic device. A computer is configured to receive an indication of the tilt of the electronic device, translate the indication of the tilt of the electronic device into a corresponding movement of the imaging plane of the medical imaging device, and transmit an instruction to the medical imaging device to cause the corresponding movement of the imaging plane. The medical imaging device may include an magnetic resonance imaging (MRI) system.

14 Claims, 4 Drawing Sheets

INTERFACE FOR MEDICAL IMAGING DEVICE

CROSS-REFERENCE TO RELATED APPLICATIONS

N/A.

STATEMENT REGARDING FEDERALLY SPONSORED RESEARCH

N/A.

BACKGROUND OF THE INVENTION

The field of the invention is systems and methods for interfacing with a medical imaging device. More particularly, the invention relates to an interactive user interface for a medical imaging device that employs a position or tilt detector to control an orientation or tilt of an imaging plane of an imaging device.

Medical imaging devices, such as magnetic resonance imaging (MRI) devices, computed topography (CT) devices, positron emission tomography (PET) devices, ultrasound devices, and the like are often used to facilitate medical procedures. During a procedure, the imaging devices allow a physician to observe the internal structures of a patient's body in order to accurately interact with one or more of those structures.

In the case of biopsies, for example, the imaging device can assist the physician in accurately penetrating a mass inside the patient with a needle in order to extract an amount of fluid or tissue therefrom. Without the imaging device, the physician may need to use an incision in the patient in order to directly observe and identify the material containing the mass.

Imaging device-guided procedures may also involve the delivery of medication or other substances to particular tissues in a patient. Brachytherapy for example, is a procedure that involves the internal delivery of radiation to a patient's tissues. The procedure can be used in the treatment of various cancers (e.g., cervical, prostate, or breast cancer). To ensure that the radiation is delivered to the correct tissue, imaging devices can be used to guide the physician in correctly positioning the radiation source. Many different procedures can be facilitated by the concurrent use of medical imaging.

Of the available imaging devices, MRI is a uniquely useful tool for prostate biopsy and brachytherapy due to MRI's capability to delineate lesions from normal tissue without exposing the patient and physician to ionizing radiation during imaging. Sometimes, the imagery generated using MRI is used only for planning and confirmation of needle placement. In other instances, however, MRI is used to acquire a cross-sectional real-time image of the procedure site from an oblique plane; with sequential two-dimensional images acquired from a plane along the needle. Such imagery allows a physician to monitor the needle with respect to the targeted lesion and adjust the needle insertion path interactively.

Unfortunately, in conventional medical imaging systems, it is difficult to position an imaging plane of the imaging device perpendicularly to the needle's path to facilitate observation. The current position of the needle must be tracked during the process. Additionally, even when the needle is numerically guided by a template or a sophisticated MRI-compatible robotic device, the trajectory of the needle may go out of the imaging plane due to positioning error or deflection of the needle.

Even though modern MRI systems allow for adjusting the orientation and position of the device's imaging plane using a graphical user interface, the physician cannot interact with the user interface in the scanner room due to the lack of portability and intuitiveness of the interface, which is often provided via a separate computer system.

Many imaging systems allow a physician to modify the imaging plane of the imaging system. Conventional systems, however, rely upon user interfaces including a conventional mouse, keyboard, and display, which are not suitable for in-theatre use (e.g., interactive imaging for interventional guidance) due to a lack of portability and do not provide a convenient interface for manipulating a two-dimensional viewing plane in three-dimensional space.

SUMMARY OF THE INVENTION

In one implementation, the present invention is a magnetic resonance imaging (MRI) system. The MRI system includes a magnet system configured to generate a polarizing magnetic field about at least a portion of a subject, a plurality of gradient coils configured to apply a gradient field to the polarizing magnetic field, and a radio frequency (RF) system configured to apply an excitation field to the subject and acquire MR image data therefrom. The MRI system includes a wireless electronic device configured to be used proximate to the magnet system and including a tilt sensor. The electronic device is configured to monitor a tilt of the wireless electronic device. The MRI system includes a computer system programmed to receive an indication of the tilt of the wireless electronic device, translate the indication of the tilt of the wireless electronic device into a corresponding operation of the plurality of gradient coils and RF system to move an imaging plane of the MRI system, and operate at least one of the plurality of gradient coils and RF system to cause the corresponding movement of the imaging plane.

In another implementation, the present invention is a system for modifying an imaging plane of a medical imaging device. The system includes an electronic device including a tilt sensor. The electronic device is configured to monitor a tilt of the electronic device. The system includes a computer configured to receive an indication of the tilt of the electronic device, translate the indication of the tilt of the electronic device into a corresponding movement of the imaging plane of the medical imaging device, and transmit an instruction to the medical imaging device to cause the corresponding movement of the imaging plane.

In another implementation, the present invention is a method of modifying an imaging plane of a medical imaging device. The method includes receiving an indication of a movement of an electronic device, translating the indication of the movement of the electronic device into a corresponding movement of the imaging plane of the medical imaging device, and transmitting an instruction to the medical imaging device to cause the corresponding movement of the imaging plane.

DETAILED DESCRIPTION OF THE INVENTION

This disclosure relates to systems and methods for interfacing with a medical imaging device. More particularly, the disclosure relates to an interactive user interface for a medical imaging device that uses a motion detector to control an orientation or tilt of an imaging plane.

The present system allows a user to manipulate a physical user interface object, such as by tilting or moving the object, to control the imaging plane of a medical imaging device. In one implementation, the user interface object includes a smartphone or other personal electronic device. The electronic device can include a display (e.g., liquid crystal display (LCD)) and has an accelerometer or gyrosensor, and wireless communication capabilities. The user interactively and intuitively adjusts the imaging plane by tilting or otherwise manipulating the orientation and/or position of the electronic device. A manipulation, tilting, or movement of the electronic device is detected by the electronic device via one or more sensors and communicated to the imaging device using a wireless communication interface. The detected manipulation of the electronic device is then translated by the imaging device into a corresponding movement of the imaging device's imaging plane (e.g., by tilting by a corresponding degree).

In one implementation, real time (or near-real time) imagery generated by the imaging device along the imaging plane is transmitted back to the electronic device, which displays the real time imagery. By displaying the real time imagery, the user is provided with feedback and can more easily make accurate changes to the imaging device's viewing plane by tilting or otherwise adjusting the position of the electronic device.

Accordingly, the present system allows a user to specify the orientation or tilt of an imaging plane of a medical imaging device in a three-dimensional space by tilting and manipulating a personal electronic device. This activity can take place in the scanner room with minimal interruption of the clinical procedure.

In various implementations, the personal electronic device is a smart phone device. Smart phone devices are widely available and may include the combination of sensors and wireless communication capabilities called for in the personal electronic device of the present disclosure. Even though this disclosure may make reference to a 'smart phone', however, any other type of electronic device including comparable sensors for detecting tilting or movement and wireless (or wired) network communications capabilities may be used instead, whether specifically configured for use in controlling medical imaging devices, or general purpose devices.

Figure 1:
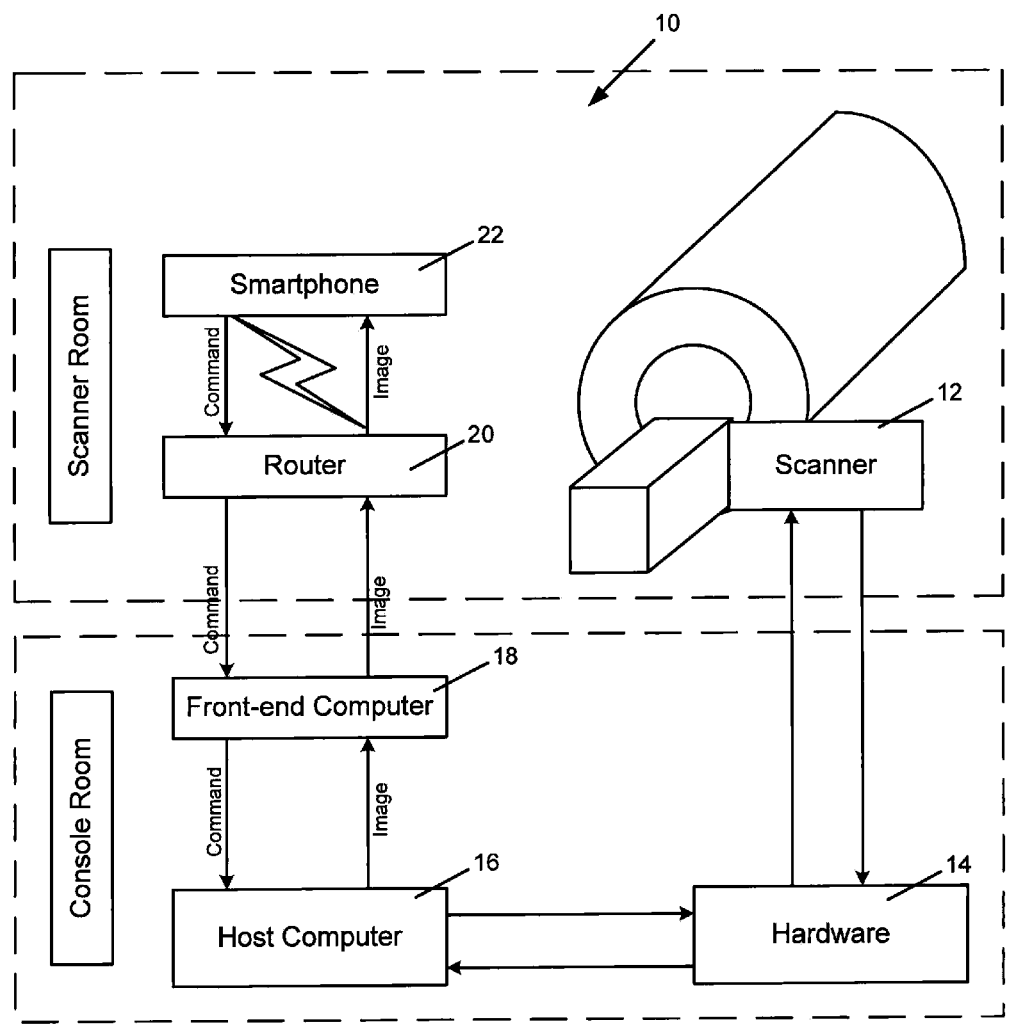
FIG. 1 is a block diagram showing components of the present system for controlling an imaging plane of an imaging device.

FIG. 1 is a block diagram showing components of the system 10 for controlling an imaging plane of an imaging device. System 10 includes medical imaging device 12, imaging device hardware 14, and an imaging device host computer 16. Imaging device 12 is configured to generate images of a slice of a subject positioned in a viewing plane of the device. In the case of an MRI, for example, the subject is positioned within the bore of the scanner to be imaged.

The imaging plane of imaging device 12 can be manipulated so as to image different portions of the subject from different angles. The imaging plane, for example, may be titled or moved. When performing a procedure upon a patient, the imaging plane is generally positioned so that the physician can observe a portion of the patient's body relevant to the procedure. This may call for the physician to position the imaging plane perpendicularly to a length of a needle being used in the procedure.

Host computer 16 is configured to interact with imaging hardware 14 to control the operation of imaging device 12 and collect data therefrom. In one implementation, medical imaging device 12, device hardware 14, and device host computer 16 are provided by an MRI system.

Front-end computer 18 includes a general-purpose personal computer configured to communicate with host computer 16. Front-end computer 18 is connected to router 20 (e.g., a WiFi router) and communicates through router 20 with electronic device 22. Electronic device 22 communicates wirelessly with front-end computer 18 through wireless router 20.

During operation of system 10, electronic device 22, imaging device 12 and, optionally, router 20 can be located within the scanner room (the location in which a procedure is ongoing). Generally, front-end computer 18, host computer 16, and imaging device hardware 14 are located outside of the scanner room in a separate console room.

Electronic device 22 may include a personal electronic device (e.g., a smartphone) and is configured to communicate wirelessly with router 20 and also to measure a tilting of electronic device 22. Electronic device 22 may also be configured to display an output that is usable by the physician to observe a current image generated along the imaging plane of the connected imaging device 12.

Figure 2:
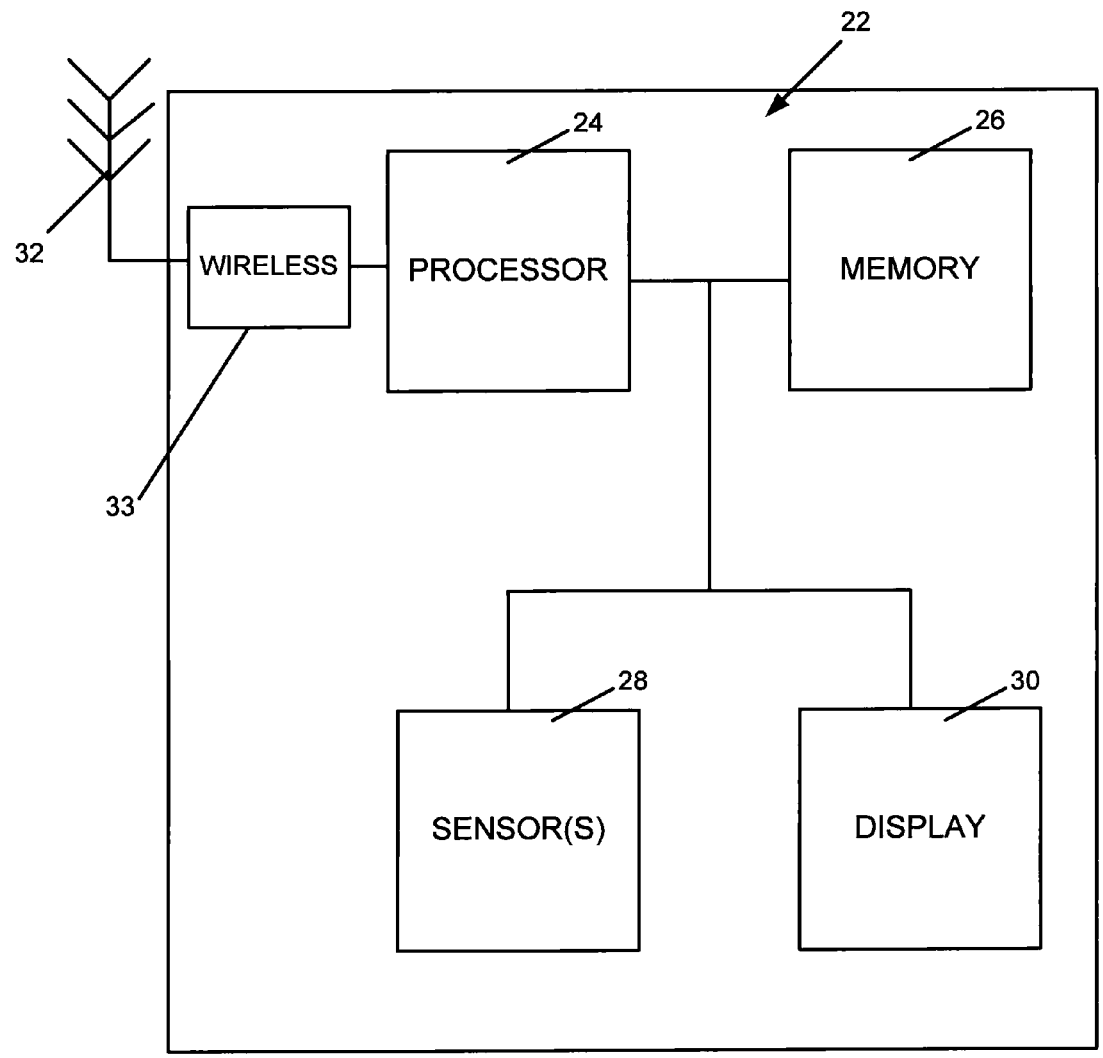
FIG. 2 is a block diagram showing functional components of an electronic device used in the system shown in FIG. 1.

FIG. 2 is a block diagram showing functional components of electronic device 22 that can be used in conjunction with system 10. In one implementation, electronic device 22 is a smart phone (e.g., an iphone). Electronic device 22 includes processor 24 in communication with memory 26. A number of instructions are stored on memory 26 to cause processor 24 to execute certain steps, as discussed below. Processor 24 is in communication with one or more sensors 28 that are configured to detect an orientation or tilt of electronic device 22. Sensors 28 may include one or more of a 3-axis accelerometer, 3-axis gyrosensor, or other sensors configured to detect one or more of a position, tilt, orientation, movement, or acceleration of an object. Electronic device 22 may incorporate additional sensor systems allowing the user to interact with electronic device 22. For example, a display of electronic device 22 may provide a touch-screen interface allowing a user to interact with electronic device 22 using finger gestures applied to the surface of the touch screen. Other conventional user interface devices, such as keyboards, trackballs, voice interfaces, and the like may also be incorporated into electronic device 22.

Electronic device 22 includes an output such as a screen or display allowing the user to view an image generated by imaging device 12 (see FIG. 1). Accordingly, processor 24 is connected to display 30 allowing information to be presented to a user. Electronic device also includes wireless communication controller 33 connected to antenna 32. Wireless communication controller 33, in combination with antenna 32, is configured to wirelessly communicate with router 20 (see FIG. 1) using any appropriate communication protocol. In other implementations, though, electronic device 22 may use a wired connection to communication with imaging device 12 (see FIG. 1). For example, a wired Ethernet connection could be established between electronic device 22 and router 20 of FIG. 1.

Returning to FIG. 1, in one implementation host computer 16 and front-end computer 18 communicate using a wired Ethernet connection (e.g., 100-base T Ethernet), while front-end computer 18 and electronic device 22 are connected using a wireless network (e.g., an IEEE 802.11n Wi-Fi network). Using these connections, information and instructions can be communicated back-and-forth between the various components of system 10 to allow electronic device 22 to both communicate instructions to imaging device 12 and receive data therefrom.

During operation of system 10, electronic device 22 provides a user interface that allows a user to interact with the imaging device 12 during real-time imaging. As the user manually manipulates electronic device 10, electronic device 10 monitors those movements using one or more sensors. The movements are then encoded and communicated to host computer 16 through router 20 and front-end computer 18 and are used by host computer 16 to manipulate the imaging plane of imaging device 12. Each tilt or movement of electronic device 22 causes a corresponding tilt or movement of the imaging plane of imaging device 12.

While electronic device 22 controls a tilting of the imaging plane of imaging device 12, images captured by imaging device 12 and processed by imaging hardware 14, host computer 16 and/or front-end computer 18 are communicated to electronic device 22 for display to the user. This provides a feedback loop allowing the user to easily manipulate the imaging plane of imaging device 12 while constantly viewing the updated imaging plane image.

The orientation and position data of electronic device 22 can be communicated to a proxy system running on front-end computer 18 over a wireless network provided by router 20. The orientation and position data can be communicated, for example, using an image and command transfer protocol (e.g., an OpenIGTLink protocol), a network communication protocol designed for image-guided therapy applications. The proxy software running on front-end computer 18 transmits commands to host computer 16 to manipulate the imaging plane of imaging device 12 using an appropriate communication protocol. Host computer 16 then updates various scan parameters to change the orientation of the imaging plane of imaging device 12.

To transmit imaging data back to the electronic device, an acquired image frame is transmitted to the proxy system of front-end computer 18 by host computer 16. The proxy system then converts the image data into a form suitable for network transfer (e.g., an image and command transfer protocol such as OpenIGTLink message), which is then transferred through router 20 to electronic device 22, where the image data can be displayed for the user.

Figure 3:
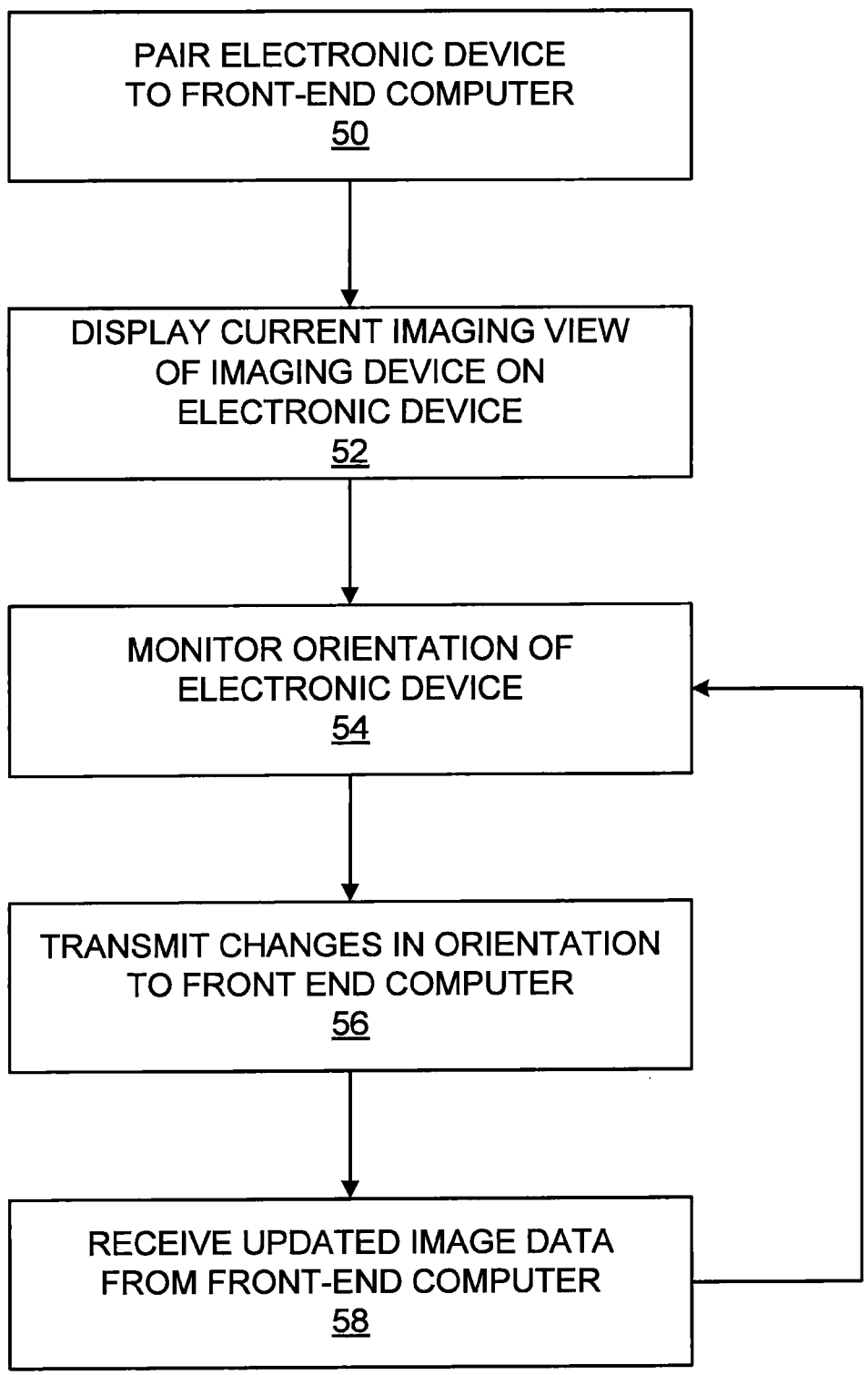
FIG. 3 is a flowchart illustrating an example method for using the present system to control a position of an imaging plane of an imaging device.

FIG. 3 is a flowchart illustrating an example method for using the present electronic device to control a position of an imaging plane of an imaging device. In step 50 the electronic device is paired (i.e., connected to) with a front-end computer for the imaging system (e.g., front-end computer 18 of FIG. 1). To ensure that electronic device 22 is paired with the correct imaging device, one or more addressing mechanisms may be used to identify both the electronic device 22 and the front-end computer of the imaging system for accurate pairing. In other cases, before pairing can complete, the user must enter a pin or other code into one or both of the front-end computer and electronic device to authorize pairing. Once paired, the electronic device can communicate with the front-end computer to transmit movement instructions to the front-end computer, which are translated into movement instructions by the front-end computer and subsequently transmitted to the imaging device. Similarly, once paired, the electronic device can receive imaging data from the front-end computer to display a current imaging view of the imaging device.

After the electronic device and front-end computer are paired, in step 52 the electronic device receives imaging data from the front-end computer depicting the current imaging plane of the imaging device. The electronic device than displays that imaging data using an appropriate user display screen. In some cases, the imaging data is compressed before transmission to improve system performance. The imaging data can include image data, matrix size, pixel size, acquisition time, position and orientation, type of imaging sequence and imaging parameters. In some cases, in addition to imaging data patient information e.g. patient name, medical record number and date of birth are transmitted to the electronic device for display.

In step 54, the electronic device uses one or more accelerometers or gyro sensors to monitor the device's orientation or tilt. As changes in the electronic device's orientation or tilt are detected, those changes are encoded and transmitted to the front-end computer in step 56. As described above, the front-end computer uses the changes to instruct the host computer to modify the imaging plane of the imaging device accordingly.

In one implementation, the changes in orientation or tilt of the electronic device are converted into a corresponding movement of the imaging plane of the imaging device in a 1:1 relationship. Accordingly, a tilt of the electronic device by 5 degrees in one direction, results in a corresponding tilt of the imaging device's imaging plane in the same direction by the same 5 degrees.

In some implementations, though, movements of the electronic device are converted into smaller corresponding movements of the imaging plane. In that case, for example, a tilt of the electronic device by 5 degrees in one direction may only cause a corresponding tilt of the imaging plane by 2.5 degrees. This reduction in effect can allow the user to make more fine-tuned movements of the imaging plane. Additionally, small movements of the electronic device that may otherwise be considered noise (e.g., small movements of the imaging device due to the user shifting their gaze away from and back to the electronic device) will not result in disruptive movements of the imaging device's imaging plane. In some cases the noise is filtered out of the movement data by either the electronic device or the front-end computer.

In addition to movements of the electronic device, additional user input, such as touch gestures (e.g., pinching or sliding) applied to a touch screen can be transmitted to the front-end computer. These additional gestures may then be used by the front-end computer to further modify the imaging plane of the imaging device, for example by zooming, or translating the imaging plane or shifting the imaging slice.

In some implementations, the user interface of the electronic device may allow the user to select from a number of different translation scales to control how movements of the electronic device are translated into corresponding movements of the imaging plane. For example, a first scale may translate small movements of the electronic device into larger movements of the imaging plane. This scale could be used to move the imaging plane quickly into the region of interest. Once in the region of interest, a second scale can be selected that translates movements of the electronic device into smaller movements of the imaging plane. This scale would be suitable to make more fine adjustments to the imaging plane. A third scale may translate movements of the electronic device into very small corresponding movements of the imaging plane. This scale would allow for very fine-scale adjustments of the imaging plane.

Additionally, the electronic device may provide a user interface (e.g., collection of buttons) allowing the user to lock certain axes of the imaging plane to limit the degrees of freedom of the imaging plane. By locking one axis, the user can provide fine control movements along a single axis without affecting the position of the imaging plane with respect to another axis.

The electronic device may provide a user interface to control whether the electronic device actively controls the imaging plane. When the electronic device is locked, movements of the electronic device have no affect upon the imaging plane. This allows, for example, physicians within the scanner room to pass the electronic device back and forth, or to put the electronic device down.

To put the electronic device into active or unlocked mode, the user interface allows a user to indicate that the electronic device should resume monitoring its current orientation or tilt. Upon turning on the device, the electronic device determines its current orientation or tilt and assigns that a zero value. From that zero value or tilt position, movements of the electronic device cause corresponding movements of the imaging plane.

Accordingly, when the electronic device is first turned on, regardless of the electronic device's current orientation or tilt, that orientation or tilt is considered to be equal to or zeroed against the current orientation or tilt of the corresponding imaging plane. From there, changes in the electronic device's orientation or tilt are communicated to the imaging device to move the imaging plane correspondingly. This behavior allows a physician to pick up the electronic device and, even without the position or tilt of the electronic device being particularly well matched to actual position or tilt of the imaging plane, use the device to make small modifications to the imaging plane. Without this behavior, the user may pick up the electronic device and begin using the electronic device without having its orientation and tilt being well matched to the imaging plane. In that case, when the electronic device begins operating (e.g., at step 54), the imaging plane may move drastically to match the current orientation and tilt of the electronic device.

Alternatively, the orientation or tilt of the imaging plane could always match that of the electronic device when the electronic device is operating. In that case, each time the electronic device begins operating, the imaging plane of the imaging device will snap or jump to match the orientation and tilt of the electronic device, even if the electronic device is being held at an awkward angle.

As changes in the orientation or tilt of the electronic device are transmitted to the front-end computer the front-end computer, in turn, transmits instructions to the imaging device to modify the orientation or tilt of the device's imaging plane accordingly. As discussed above, these instructions may involve translating the incoming movement instructions received from the electronic device to appropriately-scaled movement instructions for the imaging device.

After the orientation or tilt of the imaging plane is modified, updated image data reflecting that repositioned imaging plane is received by the electronic device in step 58. The electronic device then displays the updated image data allowing the user to see how his or her movements of the electronic device have affected the orientation or tilt of the imaging device's imaging plane.

In other implementations, the user interface may include a number of buttons or other interface mechanisms allowing the user to control additional aspects of the imaging device. For example, the electronic device may include buttons allowing for a translation or panning of the imaging plane. Similarly, the electronic device may include a number of menu options allowing different attributes or configuration settings of the imaging device to be adjusted directly from the electronic device. In some cases, a movement or translation of the electronic device is captured by the electronic device and used to control a corresponding movement or panning of the imaging plane of the imaging device.

Figure 4:
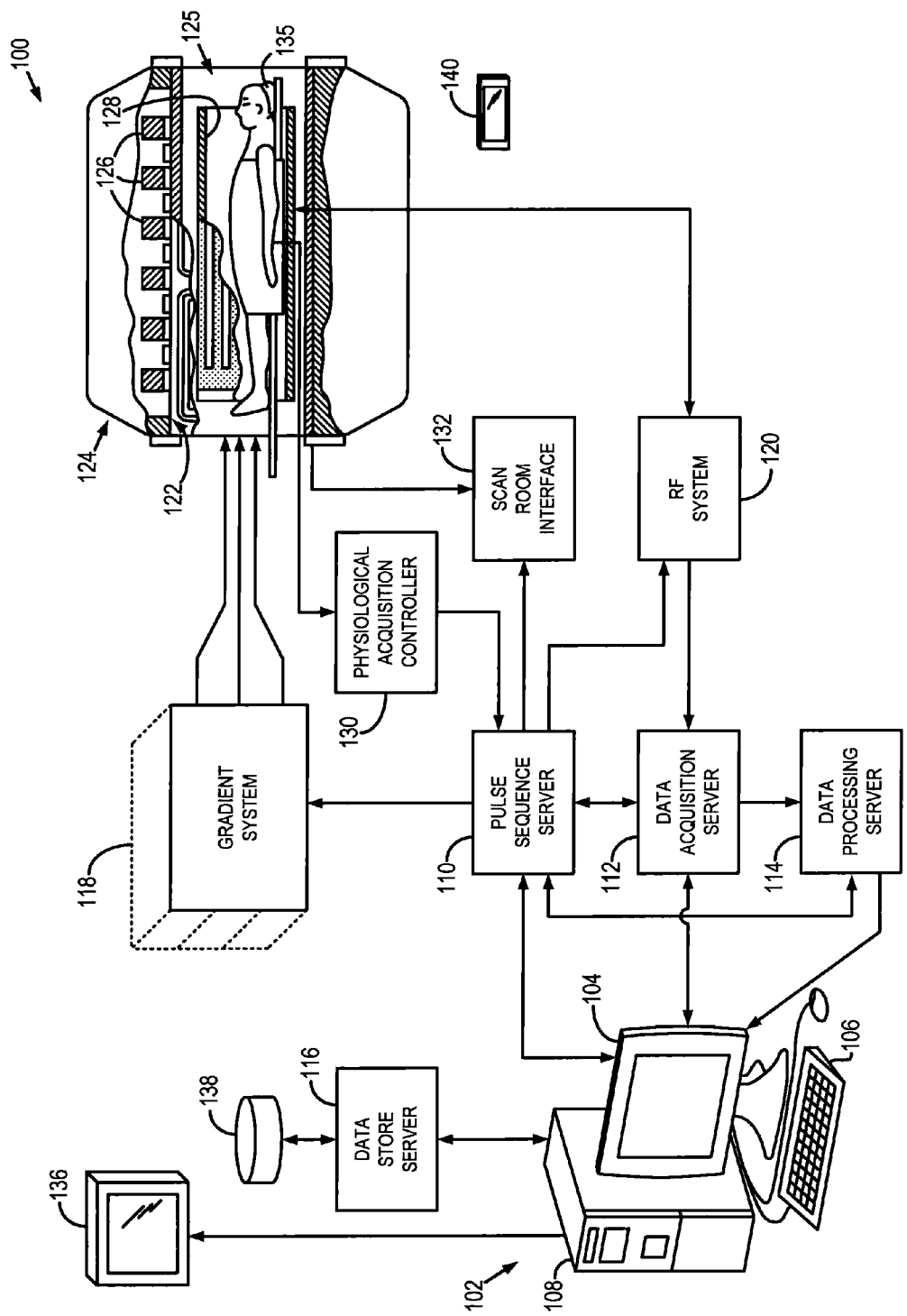
FIG. 4 depicts the functional components of an MRI system configured to communicate with an electronic device.

Referring to FIG. 4, as referenced above, the present invention can be used with a magnetic resonance imaging ("MRI") system 100. The MRI system 100 may include a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients Gx, Gy, and Gz used for position encoding MR signals. The gradient coil assembly 122 forms part of a magnet assembly 124 extending about a bore 125 formed there through and includes a polarizing magnet 126 and a whole-body RF coil 128.

RF excitation waveforms are applied to the RF coil 128, or a separate local coil (not shown), by the RF system 120 to perform the prescribed magnetic resonance pulse sequence. Responsive MR signals detected by the RF coil 128, or a separate local coil (not shown), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF amplifier that amplifies the MR signal received by the coil 128 to which it is connected, and a detector that detects and digitizes the and quadrature components of the received MR signal. The magnitude of the received MR signal may thus be determined at any sampled point by the square root of the sum of the squares of the and components:

$$M=\sqrt{I^2+Q^2} \qquad \text{Eqn. (1);}$$

and the phase of the received MR signal may also be determined:

$$\phi = \tan^{-1}\left(\frac{Q}{I}\right). \quad \text{Eqn. (2)}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Images reconstructed by the data processing server 114 are conveyed back to the workstation 102 where they are stored. Real-time images are stored in a data base memory cache (not shown), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

However, in accordance with the present invention, the images may be viewable on an electronic device 140 that is designed to be usable proximate to the magnet assembly 124. Furthermore, as explained in detail, the views provided to and the operation of the MRI system 100 to acquire MR data and reconstruct images may be controlled from the electronic device 140. For example, the electronic device 140 may translate the indication of the tilt of the electronic device 140 into a corresponding movement of the imaging plane of the images acquired and reconstructed by the MRI system 100. To do so, the electronic device 140 itself may transmit an instruction to the MRI system, for example, by communicating with the workstation 102, pulse sequence server 110, data acquisition server 112, and/or data processing server 114 to cause the corresponding movement of the imaging plane. Alternatively, the electronic device 140 may simply communicate user inputs received at the electronic device 140, such as a tilt input, and the workstation 102, pulse sequence server 110, data acquisition server 112, and/or data processing server 114 translates the communicated user inputs to a responsive control of the MRI system 100.

In implementations of the present system using the electronic device 140, when embodied as a smart phone, to provide the functionality of the electronic device, it is important to consider whether the electromagnetic signals emanating from the smart phone could disrupt the electromagnetic signals used by the MRI system 100. Accordingly, an investigation was performed to determine the degree to which signals emanating from a smart phone could affect a medical imaging device.

One such investigation involved the scanning of a liquid phantom using an MRI device. A Wi-Fi router (AirPort Extream, Apple Inc., Cupertino, Calif.) was placed at the corner of the scanner room, outside of the 5 gauss line and 5.7 meters (m) away from the isocenter of the magnet of the MRI device. The router and the smartphone were wirelessly connected using the IEEE 802.11n (2.4 gigahertz (GHz)) communications standard. Interactive real-time imaging was performed with the MRI using a research prototype True-FISP-based BEAT-IRTTT sequence (TR/TE: 3.96/1.98 millisecond (ms); Matrix size: 128×128; Flip angle: 45 degrees; FOV: 200×200 square millimeters (mm2), In-plane pixel size: 1.6×1.6 mm2; Slice thickness: 5 millimeters (mm); Pixel bandwidth 908 hertz per pixel (Hz/pixel)). The frame rate of the imaging was 2 frames per second (fps).

During the investigation a user tilted the smartphone device randomly at a location 2.1 m away from the isocenter of the MRI system during imaging, approximately on the 200-gauss line. Signal-to-noise ratio (SNR) of the image was measured 1) without the Wi-Fi router and the smartphone in the scanner room, 2) with only the Wi-Fi router in the room, and 3) while controlling the scanner using the smartphone with the above mentioned setting.

In this investigation, the signal to noise ratio (SNR) of the real-time images under conditions 1)-3) were 147.4, 154.4 and 159.7 respectively. These measured SNR are acceptable as they do not significantly exceed baseline measured SNRs for installations that do not include a wireless router or electronic device configured as described herein. Because there is no significant change to the SNR, any interference introduced by the router and electronic device is negligible and not disruptive to the imaging process.

In implementations of the system where the electronic device is configured to provide feedback to the user in the form of updated images of the imaging device's imaging plane, it is also important to consider the latency of the system. Accordingly, an investigation can be performed to evaluate the latency of the interactive imaging plane control and image transfer of the present system.

In the investigation, the orientation information transmitted to the imaging device from the electronic device, and the images received by the electronic device from the imaging device were recorded with timestamps obtained from the internal clock of the smartphone. Accordingly, a timestamp was obtained at the time at which instructions to modify the imaging device's imaging plane were transmitted by the electronic device and the time at which updated images from the imaging device were received by the electronic device. In the investigation 36 real-time images were acquired.

Debugging information was then extracted from the smartphone via Universal Serial Bus using a debugger (XCode 4.2, Apple Inc, Cupertino, Calif.). The recorded timestamps were then analyzed to measure the time between the change of the orientation of the smart phone and the corresponding change of the imaging plane appearing in the image displayed by the smart phone.

In this investigation, the measured latency was 0.78±0.05 s.

The present system, therefore, allows for the control of an imaging plane of a medical imaging device using an electronic device, such as a smart phone, equipped with an accelerometer and gyrosensor. The electronic device allows an operator to specify the imaging plane interactively in the scanner room while imaging is ongoing. The electronic device can be used in a sterile environment (such as that required during execution of a procedure) in the hand of a physician if the electronic device is covered with a plastic bag or other suitable container. As changes in the imaging plane follow from corresponding changes in the orientation or tilt of the electronic device, and the image by the imaging device is visualized on the electronic device's screen simultaneously, the present system provides a closed loop of control and monitoring. The system, therefore, greatly facilitate the manipulation of an imaging plane by a user. This could allow, for example, for an operator to more easily search for a needle, especially when the needle is deflected, during a procedure.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
   a magnet system configured to generate a polarizing magnetic field about at least a portion of a subject;
   a plurality of gradient coils configured to apply a gradient field to the polarizing magnetic field;
   a radio frequency (RF) system configured to apply an excitation field to the subject and acquire MR image data therefrom;
   a wireless electronic device configured to be used proximate to the magnet system and including a tilt sensor, the wireless electronic device being configured to monitor a tilt of the wireless electronic device; and
   a computer system programmed to:
      receive an indication of the tilt of the wireless electronic device,
      receive, via a user interface of the wireless electronic device, a selection of one of a plurality of translation scales, each one of the plurality of translation scales for translating the indication of the tilt of the wireless electronic device into different movements of an imaging plane of the MRI system,
      determine, using the indication of the tilt of the wireless electronic device and the selection of the one of the translation scales, a corresponding movement operation of the plurality of gradient coils and RF system to move the imaging plane of the MRI system, and
      operate at least one of the plurality of gradient coils and RF system to cause the corresponding movement of the imaging plane.

2. The MRI system of claim 1, wherein the computer system is configured to:
   receive updated imaging data from the MRI system; and
   transmit the updated imaging data to the wireless electronic device.

3. The MRI system of claim 2, wherein the wireless electronic device includes a display screen and the wireless electronic device is configured to display the updated imaging data.

4. The MRI system of claim 1, wherein the wireless electronic device includes a smart phone.

5. The MRI system of claim 1, wherein the computer system is configured to communicate using an image and command transfer protocol.

6. A system for modifying an imaging plane of a medical imaging device, comprising:
   an electronic device including a tilt sensor, the electronic device being configured to monitor a tilt of the electronic device; and
   a computer configured to:
      receive an indication of the tilt of the electronic device,
      receive a selection of one of a plurality of translation scales,
      translate the indication of the tilt of the electronic device into a corresponding movement of the imaging plane of the medical imaging device using the one of the plurality of translation scales, and
      transmit an instruction to the medical imaging device to cause the corresponding movement of the imaging plane.

7. The system of claim 6, wherein the electronic device includes a wireless communication module and the electronic device and the computer are configured to communicate wirelessly.

8. The system of claim 6, wherein the computer is configured to:
   receive updated imaging data from the medical imaging device; and
   transmit the updated imaging data to the electronic device.

9. The system of claim 8, wherein the electronic device includes a display screen and the electronic device is configured to display the updated imaging data.

10. The system of claim 6, wherein the electronic device includes a smart phone.

11. The system of claim 6, wherein the computer is configured to communicate using an image and command transfer protocol.

12. A method of modifying an imaging plane of a medical imaging device, comprising:
   receiving an indication of a movement of an electronic device;
   identifying one of a plurality of translation scales, each one of the plurality of translation scales for translating the indication of the movement of the electronic device into different movements of the imaging plane of the medical imaging device;
   translating the indication of the movement of the electronic device into a corresponding movement of the imaging plane of the medical imaging device using the one of the plurality of translation scales; and
   transmitting an instruction to the medical imaging device to cause the corresponding movement of the imaging plane.

13. The method of claim 12, including receiving updated imaging data from the medical imaging device.

14. The method of claim 13, including transmitting the updated imaging data to the electronic device.

* * * * *